(12) United States Patent
Schlichter

(10) Patent No.: US 7,614,121 B2
(45) Date of Patent: Nov. 10, 2009

(54) APPARATUS FOR MEASURING THE MASS OF FIBRE MATERIAL PASSING THROUGH A SPINNING PREPARATION MACHINE OR SYSTEM

(75) Inventor: Stefan Schlichter, Viersen (DE)

(73) Assignee: Trützschler GmbH & Co. KG, Monchengladbach (DE)

( * ) Notice: Subject to any disclaimer, the term of this patent is extended or adjusted under 35 U.S.C. 154(b) by 671 days.

(21) Appl. No.: 11/158,016

(22) Filed: Jun. 22, 2005

(65) Prior Publication Data
US 2006/0010655 A1 Jan. 19, 2006

(30) Foreign Application Priority Data
Jun. 26, 2004 (DE) ............ 10 2004 030 967

(51) Int. Cl.
*D01G 15/40* (2006.01)
(52) U.S. Cl. .................................................. 19/105
(58) Field of Classification Search .................. 19/105
See application file for complete search history.

(56) References Cited

U.S. PATENT DOCUMENTS 6,360,403 B1 * 3/2002 Rubenach ............... 19/97.5
2002/0026688 A1 * 3/2002 Rubenach ............... 19/97.5
2002/0116792 A1 * 8/2002 Pinto ...................... 19/105
2003/0097830 A1 5/2003 Herrmann et al.
2003/0150266 A1 8/2003 Dammig et al.
2004/0060352 A1 4/2004 Cherif et al.

FOREIGN PATENT DOCUMENTS

| DE | 201 19 344 U1 | 5/2003 |
| EP | 1 371 979 A1 | 12/2003 |
| GB | 2 400 443 A | 10/2004 |
| WO | WO 00/12974 A1 | 3/2000 |
| WO | WO 00/55606 A3 | 9/2000 |
| WO | WO 2004/001110 A1 | 12/2003 |

* cited by examiner

*Primary Examiner*—Shaun R Hurley
(74) *Attorney, Agent, or Firm*—Venable LLP; Robert Kinberg; Ryan M. Flandro

(57) ABSTRACT

In an apparatus for measuring the mass of fibre material passing through a spinning preparation machine or system or through a nonwoven production device, at least one microwave resonator is provided. In order to improve measurement of the mass of fibre material in a cleaning system, especially between a bale opener and carding machine, and to use that measurement for closed-loop and/or open-loop control, the fibre material is present in the form of fibre flocks and the fibre flocks pass through a measurement pathway having a measuring device having the at least one microwave resonator.

28 Claims, 4 Drawing Sheets

APPARATUS FOR MEASURING THE MASS OF FIBRE MATERIAL PASSING THROUGH A SPINNING PREPARATION MACHINE OR SYSTEM

CROSS REFERENCE TO RELATED APPLICATION

This application claims priority from German Patent Application No. 10 2004 030 967.1 dated Jun. 26, 2004, the entire disclosure of which is incorporated herein by reference.

BACKGROUND OF THE INVENTION

The invention relates to an apparatus for measuring the mass of fibre material passing through a spinning preparation machine or system or through a nonwoven production device.

In a known apparatus (WO 00/12974), a carding machine is provided wherein unprocessed crude fibre material enters the carding machine at a slow speed and carded fibre material in the form of a fibre sliver or fibre web leaves the carding machine at a high speed. The carded fibre material passes through a microwave resonator, which is arranged at the exit from the carding machine and which measures the mass (density) of the fibre material. That measurement value is suitable for fine regulation of the carded fibre material, which forms an intermediate product. Furthermore, at the entrance to the carding machine there is optionally provided a measuring device for the moisture content of the unprocessed crude fibre material; this is intended to allow rough regulation. A substantial disadvantage is that rough regulation does not allow precise and uniform flows of fibre material to be accomplished in the cleaning system upstream of the carding machine. For example, the production of fibre blends having exact proportions of different fibre components is not possible using the known apparatus.

It is an aim of the invention to provide an apparatus of the kind described at the beginning that avoids or mitigates the mentioned disadvantages and, especially, that makes it possible to improve measurement of the mass of fibre material in a cleaning system, especially between a bale opener and carding machine, and to use that measurement for closed-loop and/or open-loop control.

SUMMARY OF THE INVENTION

The invention provides an apparatus for determining the mass of textile fibre material in the form of fibre flocks, comprising:

a measurement pathway for the fibre flocks; and a measuring device comprising at least one microwave resonator for monitoring flocks in the measurement pathway.

The measures according to the invention make it possible to accomplish precise and uniform flows of fibre material in a cleaning machine or cleaning system. The measurement of the mass of the fibre flocks, especially with compensation for the moisture content, can be used for open-loop and/or closed-loop control. It is possible, especially, for relatively large to large amounts of fibre material, as are processed in a cleaning system, to be measured precisely. Furthermore, the invention makes it possible for fibre material to be dispensed in exact amounts. A particular advantage is that the apparatus according to the invention makes it possible, by simple means, for the fibre mass of different fibre components to be ascertained in non-contacting manner, as a result of which fibre blends of exact proportions, for example 60% cotton and 40% polyester, can be produced.

Advantageously, the moisture content of the fibre flocks can be measured. Advantageously, it is possible to compensate for the moisture content when measuring the mass of the fibre flocks. Advantageously, the measurement value of the mass of the fibre flocks is used for open-loop control of at least one spinning preparation machine. Advantageously, the measurement value of the mass of the fibre flocks is used for closed-loop control of at least one spinning preparation machine. Advantageously, the measurement value of the mass of the fibre flocks is used for dispensing in metered amounts in the course of feeding a spinning preparation machine. Advantageously, the measurement value of the mass of the fibre flocks is used for feeding a conveying device, for example, a conveyor belt, chute or the like. Advantageously, the measurement value of the mass of the fibre flock is used for feeding a transporting device, for example, a pneumatic flock-transporting device, pipeline, shaft or the like. Advantageously, the measuring device is arranged at the exit from a hopper feeder. The hopper feeder may have a driven conveyor belt, for example, an ascending needled lattice. A driven stripping device, for example, a smoothing cylinder, may be associated with the conveyor belt of the hopper feeder. The speed of the inclined lattice of the hopper feeder may be adjustable. The speed of the stripper roller of the hopper feeder may be adjustable. The measuring device may be associated with a conveying device, for example, a conveyor belt, chute or the like. The measuring device may be arranged at the exit from a condenser. The measuring device may be associated with a flock charging shaft. The measuring device may be arranged downstream of at least one slow-speed take-off roller of the condenser and/or of the flock charging shaft. The speed of the at least one take-off roller of the flock charging shaft may be adjustable. Advantageously, the measuring device is arranged downstream of a high-speed opener roller. Advantageously, the opener roller is arranged downstream of the at least one take-off roller. Advantageously, a driven conveyor belt is arranged downstream of the hopper feeder. The speed of a conveyor belt arranged downstream of the at least one hopper feeder may be adjustable. Advantageously, a driven conveyor belt is arranged downstream of the flock charging shaft. The speed of the conveyor belt arranged downstream of the at least one flock charging shaft may be adjustable.

In one preferred embodiment, the fibre flocks pass through the microwave resonator in flight, for example, they may be carried through the resonator by a pneumatic transport system. In another preferred embodiment, the fibre flocks fall through the microwave resonator.

In the case of formation of a fibre blend, means for dispensing prespecifiable amounts of fibre flocks of different grades may be provided. Advantageously, the fibre flocks of the blend components are introduced into charging shafts of a mixing apparatus and are in each case deposited at the lower end of a charging shaft onto a conveyor belt (mixing belt) by at least one take-off roller. Advantageously, the conveyor belt (mixing belt) is arranged to be driven in variable manner.

Advantageously, the fibre mass is arranged to be measured continuously. Advantageously, the fibre feed is carried out continuously. For mixing, closed-loop volumetric flow control may be provided.

In one embodiment, the measurement value of the mass of the fibre flocks is used for open-loop control and/or closed-loop control of a cleaning system having at least two cleaning machines, preferably a plurality of cleaning machines.

In a second embodiment, the measurement value of the mass of the fibre flocks is used for open-loop control and/or closed-loop control of a carding system having at least one carding machine, preferably a plurality of carding machines.

In a third embodiment, the measurement value of the mass of the fibre flocks is used for determining the through-flow rate in a pipeline or the like for conveying fibre material. Conveying of the fibre flocks may be carried out pneumatically. The apparatus may be used for determining the through-flow rate in a pipeline or the like for fibre waste.

The measurement value of the mass of the fibre flock may be used for determining production in a flock charging shaft. The measurement value of the mass of the fibre flocks may be used for determining production in a flock mixer, for example, a multi-mixer. The measurement value of the mass of the fibre flocks may be used for determining production in a flock feeder, for example, having an upper reserve shaft and a lower feeding shaft. Mixing of the fibre material components may be carried out in the air flow.

The invention also provides an apparatus for measuring the mass of fibre material passing through a spinning preparation machine or system or through a nonwoven production device, wherein at least one microwave resonator and an associated measurement electronics unit matched thereto are provided, in which the fibre material is present in the form of fibre flocks and the fibre flocks pass through a measurement pathway having a measuring device having the at least one microwave resonator.

Moreover, the invention provides a method for measuring the mass of fibre material in flock form, comprising causing the fibre flocks to pass through a measurement zone and determining a parameter relating to mass of the fibre in the measurement zone by means of a measuring device comprising at least one microwave resonator.

The terms "measurement of the fibre mass", "fibre flock mass" or the like also include the measurement of equivalent parameters such as, especially, the flock density, the flock weight and the like and also variations in those parameters.

DETAILED DESCRIPTION OF PREFERRED EMBODIMENTS

Figure 1A:
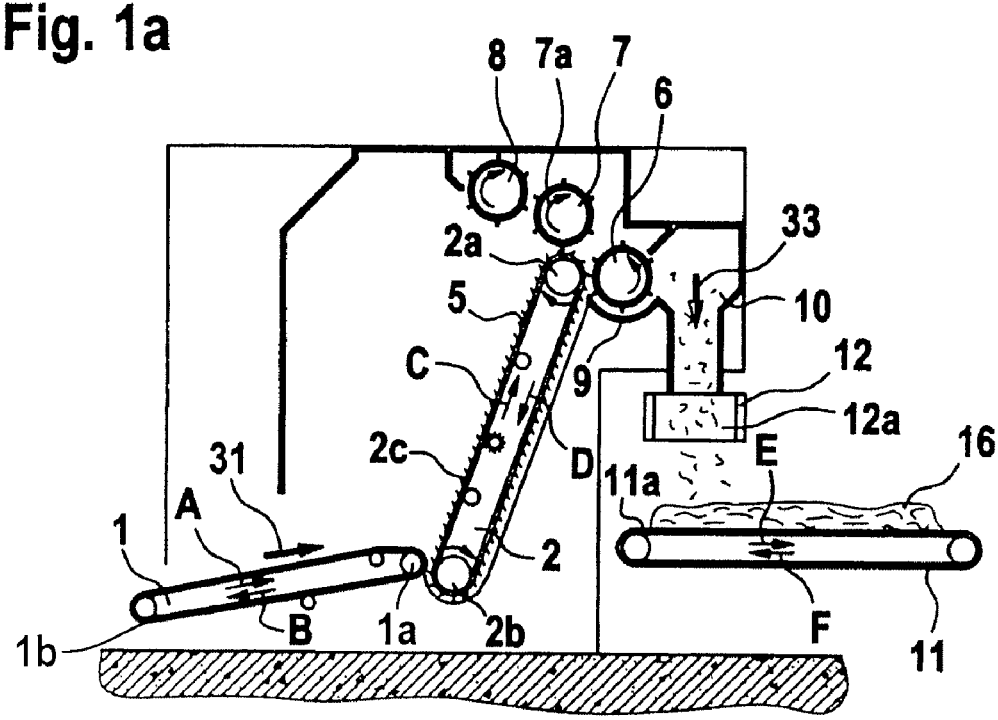
FIG. 1a is a diagrammatic side view of a bale opener (hopper feeder) with a delivery conveyor belt, wherein a first embodiment of the invention is arranged downstream of the inclined lattice and stripping roller.
Figure 7:
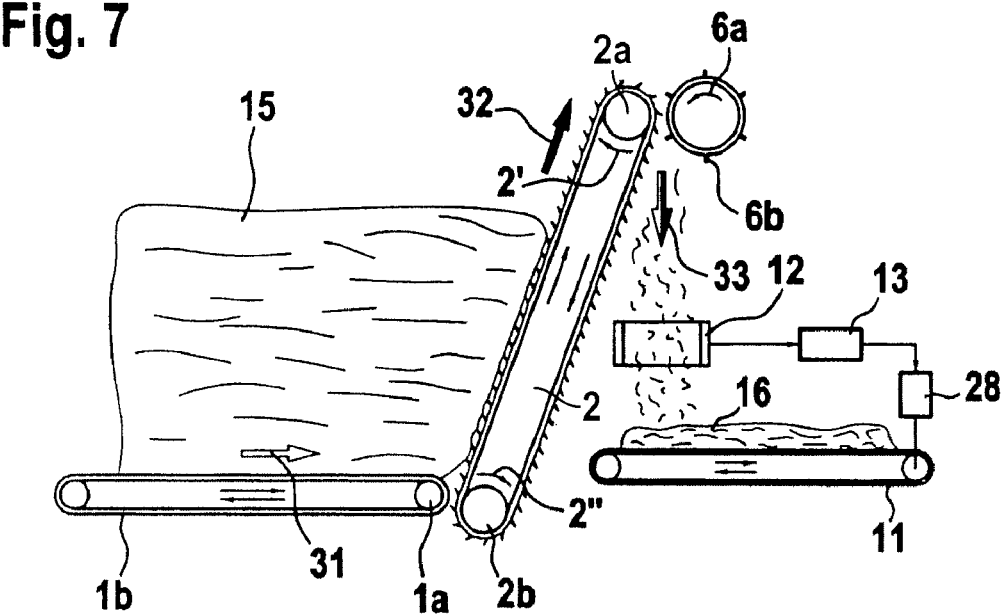
FIG. 7 shows a bale opener (hopper feeder) and delivery conveyor belt according to FIG. 1a, in which an apparatus according to the invention is used for open-loop control of the delivery conveyor belt.
Figure 8:
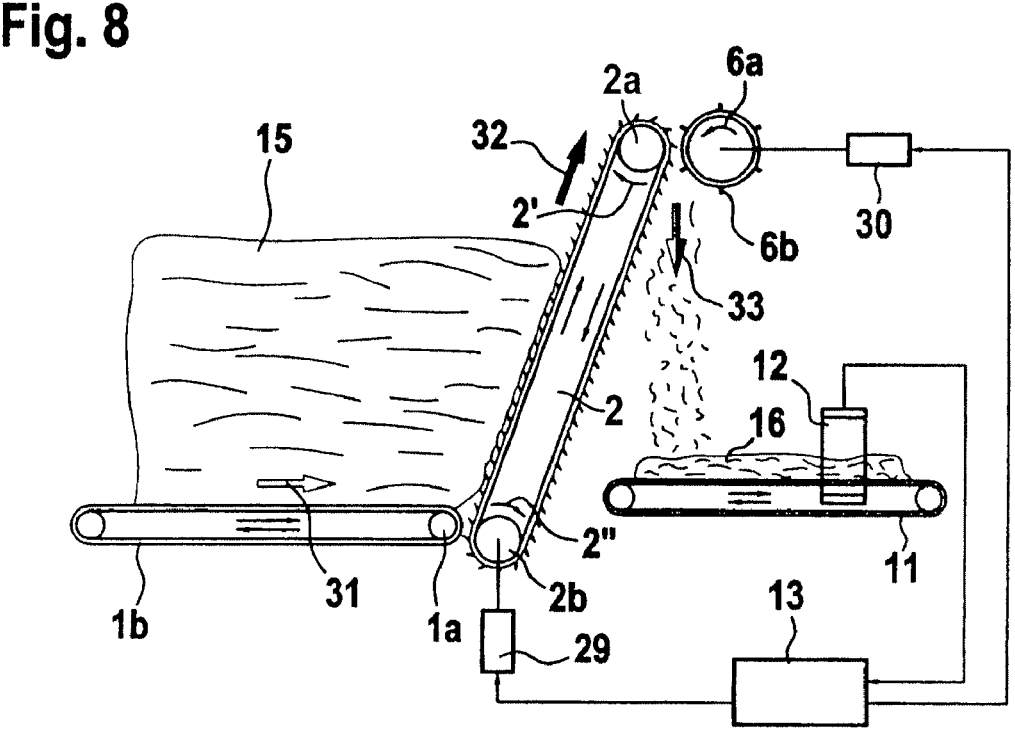
FIG. 8 shows a bale opener (hopper feeder) and delivery conveyor belt according to FIG. 1b, wherein the apparatus according to the invention is used for closed-loop control of the drive motors of the inclined lattice and stripping roller.

With reference to FIG. 1a, an apparatus for operation of a feeding device for fibre material, for example a BO-U Universal Bale Opener made by Trützschler GmbH & Co. KG of Mönchengladbach, Germany has an upwardly inclined feed table 1 in the form of a conveyor belt 1b endlessly revolving in directions A, B about a roller 1a. The feed table 1 feeds the fibre material 15 (not shown in FIG. 1, but see FIGS. 7-8) in a direction 31 to a needle table 2, which includes a needled lattice 2c endlessly revolving around return rollers 2a, 2b in directions C, D. The return rollers 2a, 2b rotate in the direction of the arrows 2' and 2", respectively (see FIGS. 7, 8). With the aid of the needles 5, the fibre material 15 is conveyed in direction C (or direction 32 as shown in FIGS. 7 and 8) and is passed around the upper return roller 2a. Arranged downstream of the upper return roller 2a and approximately horizontal in relation thereto is a stripping roller 6, the direction of rotation 6a of which is opposite the direction of rotation 2' of the return roller 2a. The stripping roller 6 is provided with needles 6b and strips the fibre material off the needled lattice 2c and conveys it along a guide 9 towards a feed element 10 partly in the shape of a funnel, below which there is arranged a conveyor belt 11. endlessly revolving in directions E, F. Arranged between the exit from the feed element 10 and the upper belt region 11a of the delivery conveyor belt 11 is a measuring device 12 having a microwave resonator (microwave measuring apparatus). The fibre flocks 33 pass through the measuring device 12 in flight, whereupon the mass of the fibre flocks 33 passing through is ascertained. The measuring device 12 is in communication electrically with an electronic control and regulation device 13 (see FIGS. 7 and 8). The fibre flocks 33 fall through the air (fibre/air mixture) onto the belt region 11a. Reference numeral 7 denotes a retaining roller rotating in a direction of rotation 7a and reference numeral 8 denotes a stripping roller for the retaining roller 7. The mass of the fibre flocks 33 is measured in the air flow.

Figure 1B:
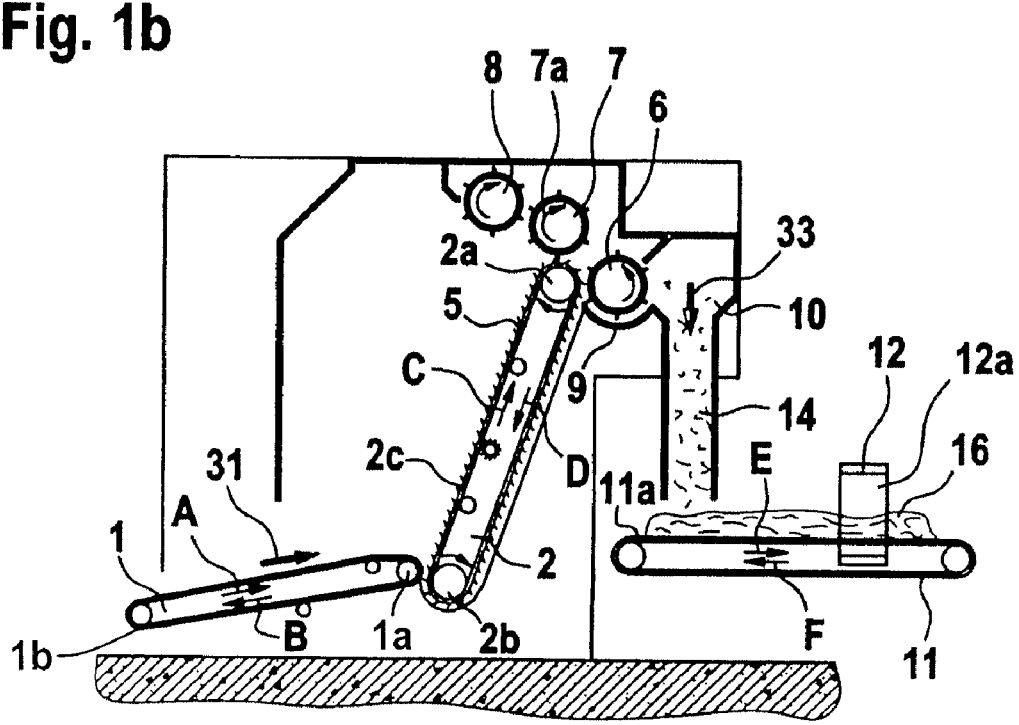
FIG. 1b shows a bale opener (hopper feeder) and delivery conveyor belt, wherein a second embodiment of the invention is associated with the delivery conveyor belt.

In accordance with FIG. 1b, downstream of the feed element 10 there is arranged a feed shaft 14, which deposits the fibre flocks 33 on the upper belt region 11a of the delivery conveyor belt 11 in the form of a loose (open) flock layer 16. The fibre flocks 33 fall through the feed shaft 14 (fibre/air mixture). The measuring device 12 is associated with the delivery conveyor belt 11 in such a manner that the upper belt region 11a together with the flock layer 16 passes through the interior 12a of the measuring device 12 in the direction of arrow E. The mass of the fibre flocks 16 is measured on the delivery conveyor belt 11 (which can have a closed surface or which can be in the form of a perforated belt).

Figure 2:
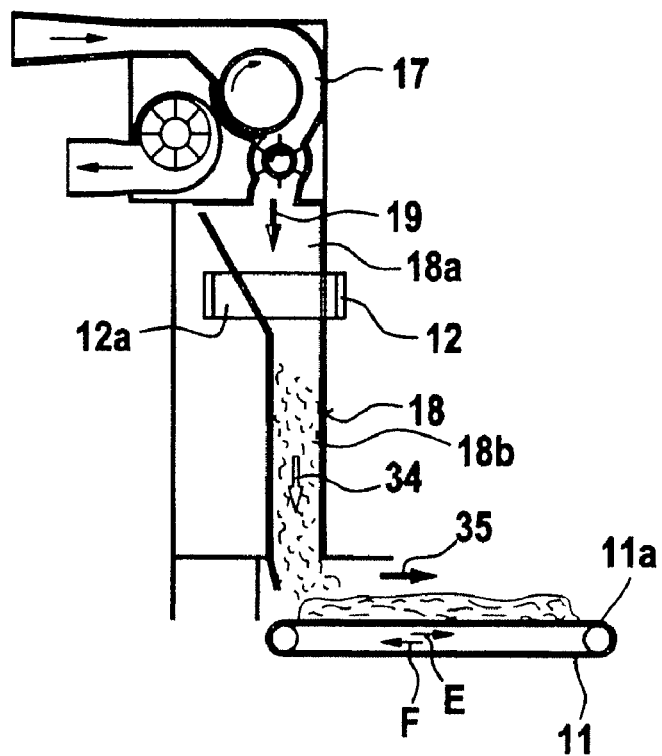
FIG. 2 is a side view of a condenser with a further embodiment of the invention, arranged downstream of the condenser.

In accordance with FIG. 2, there is provided a feed arrangement having a shaft, wherein a delivery conveyor belt 11 is fed by a condenser 17 and a feed shaft, for example, a FD-T Feed Shaft 18 made by Trü, tzschler GmbH & Co. KG. The fibre flocks 19 delivered by the condenser 17 fall through the funnel-shaped upper entry region 18a in direction 34 and into the lower feed region 18b, where they are deposited, arriving on the upper belt region 11a of the delivery conveyor belt 11 to be moved in a direction 35. The measuring device 12 (microwave measuring apparatus) is associated with the entry region 18a in such a manner that the mixture of fibre flocks 19 and air passes through the interior 12a of the measuring device 12, whereupon the mass of the fibre flocks 19 in the air flow is measured.

Figure 3:
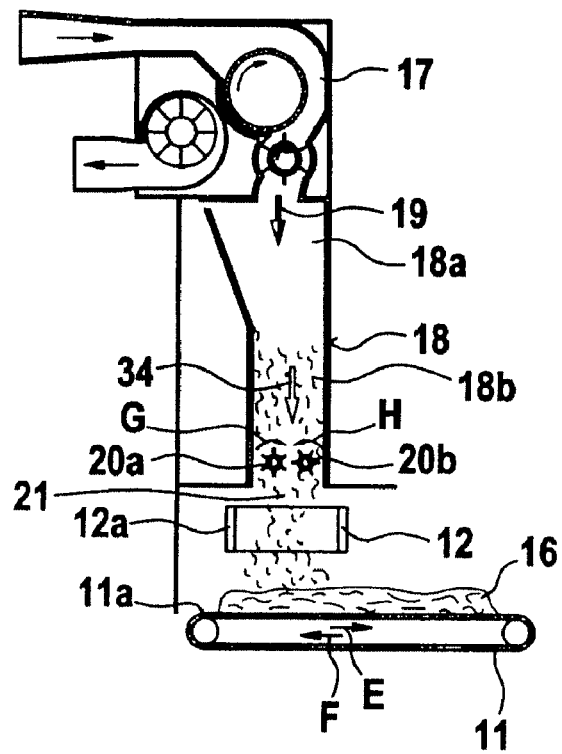
FIG. 3 is a side view of a flock charging shaft having take-off rollers, wherein an apparatus according to the invention is arranged downstream of take-off rollers.

In accordance with FIG. 3, at the lower end of the feed region 18b (which has vertically arranged, parallel wall surfaces) of the feed shaft 18 there are arranged two take-off rollers 20a, 20b slowly rotating in opposite directions (see arrows G, H), which remove fibre flocks 21 from the feed shaft 18. A measuring device 12 is arranged beneath the take-off rollers. The fibre flocks 21 pass through the interior 12a of the measuring device 12 (microwave measuring apparatus) in the form of a mixture of fibre flocks 21 and air and arrive on the upper belt region 11a of the delivery conveyor belt 11, where they are deposited in the form of a flock layer 16. The mass of the fibre flocks 21 is measured in the air flow.

Figure 4:
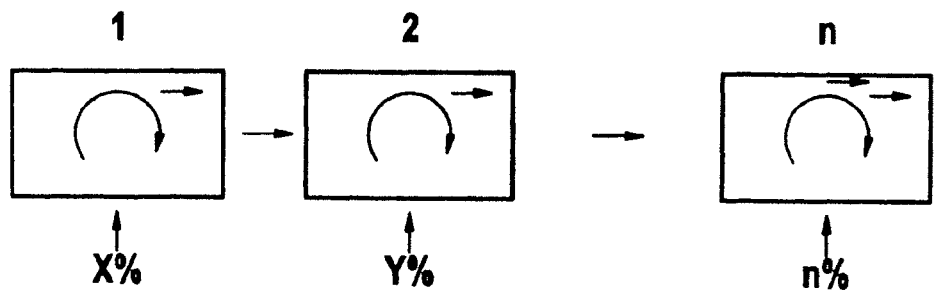
FIG. 4 is a diagram of a mixing system for producing blends of different fibre material components.

FIG. 4 is a diagram of a mixing system comprising a plurality of mixing devices, in which different grades (or types or components) of fibre material 1 to n are processed to form a fibre blend. In accordance with the desired mixing ratio in the blend to be produced, there are provided x % of fibre component 1, y % of fibre component 2 and n % of fibre component n. For example, a blend of 60% cotton and 40% polyester can be produced.

Figure 5:
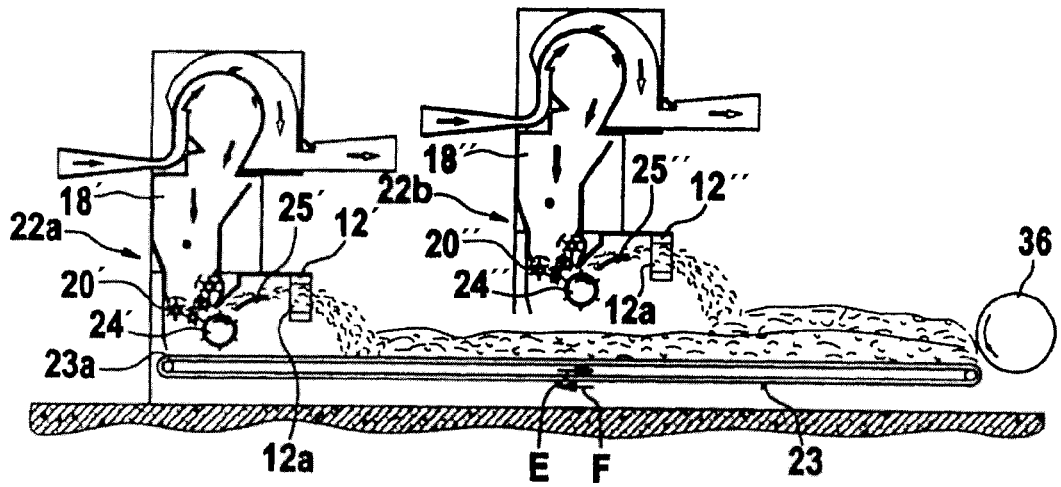
FIG. 5 shows two feeding devices with an opener or cleaner, each with a respective apparatus according to the invention, and a common flock mixing belt, for example for two fibre material components.

In accordance with FIG. 5, there is provided a feed apparatus for two fibre material components, wherein two feed devices 22a, 22b deliver different fibre material components to a common flock mixing belt 23 arranged below them. Each of the feed devices 22a, 22b has a feed shaft 18' and 18'', respectively, four take-off rollers 20' and 20'', respectively, and a high-speed opener or cleaning roller 24' and 24'', respectively. Arranged downstream of each of the opener or cleaning rollers 24', 24'' is a measuring device (microwave measuring apparatus) 12' and 12'', respectively, so that the fibre flocks 25' and 25'', respectively, pass through the particular interior 12a of, respectively, device 12' or 12'', in flight or in the air flow and are then deposited in the form of layers (two layers) on top of one another on the upper belt region 23a of the flock mixing belt 23. Associated with the end (seen in direction E) of the flock mixing belt 23 is a high-speed roller 36, which takes off and disperses the two flock layers.

Figure 6:
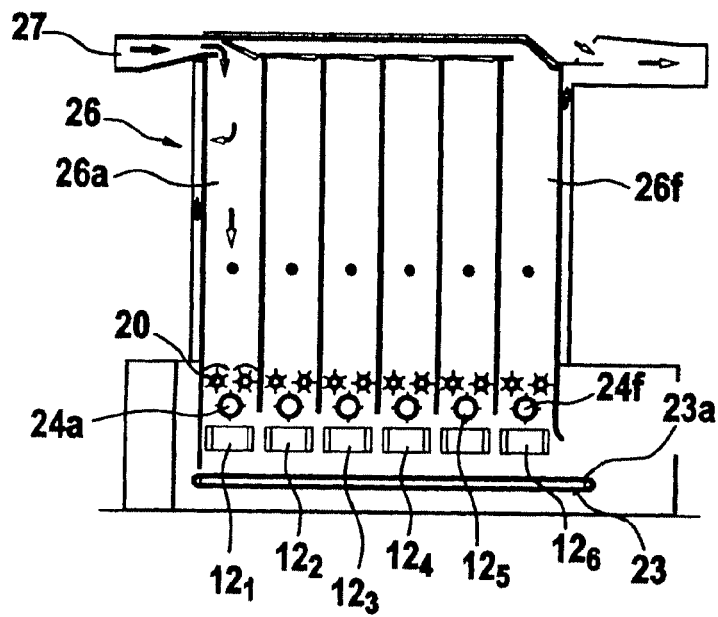
FIG. 6 shows a multiple mixer, wherein an apparatus according to the invention is associated with each charging shaft.

The multiple mixer 26 according to FIG. 6, for example a MX-I Integrated Mixer made by Trützschler GmbH & Co. KG, has six charging shafts 26a to 26f pneumatically fed with fibre flocks 27, at the lower end of each of which shafts there is arranged a pair of take-off rollers 20 (see elements 20a, 20b in (FIG. 3) and a high-speed opener roller 24a to 24f (see FIG. 5). The opener rollers 24a to 24f deliver the opened fibre flocks onto a common flock mixing belt 23, on the upper belt region 23a of which six layers of six different fibre material components are deposited (not shown). Arranged between each of the opener rollers 24a to 24f and the upper belt region 23a, that is to say below the opener rollers 24a to 24f and above the belt region 23a, there is a measuring device $12_1$ to $12_6$, through the interior 12a of a respective one of which the opened fibre flocks pass, whereupon their mass is measured. The measuring devices $12_1$ to $12_6$ are connected to the electronic control and regulation device 13 (see FIGS. 7, 8). By that means, in accordance with the mixing principle shown in FIG. 4, a fibre blend can be produced with exact proportions of particular different fibre components by means of open-loop control (see FIG. 7) or closed-loop control (see FIG. 8).

In accordance with FIG. 7, the measuring device 12 is in communication with an open-loop-controlled drive motor 28 by way of the electronic control and regulation device 13. In accordance with FIG. 8, the measuring device 12 is in communication with the closed-loop-controlled drive motor 29 for the inclined needle table 2 and with the closed-loop-controlled drive motor 30 for the stripping roller 6. The arrangements shown in FIGS. 7 and 8 form an open-loop-controlled dispensing device and a closed-loop-controlled dispensing device, respectively, in each case delivering fibre flocks 33 onto a delivery conveyor belt 11. A plurality of such dispensing devices, that is to say a plurality of delivery conveyor belts 11a to 11n (not shown) can each deliver different fibre material components in desired proportions onto a common flock mixing belt 23 (see FIGS. 5 and 6), in order to produce a fibre blend of predetermined proportions.

The apparatus according to the invention comprises at least one microwave sensor 12, 12', 12'', $12_1$ to $12_6$ for measuring a dielectric property, especially a property related to the mass of the fibre flocks, using a microwave resonator, the flocks 16, 19, 21, 25', 25'', 33 introduced into the resonator interacting with a resonant microwave field produced in the resonator in order to ascertain suitable measurement parameters indicative of the mass of the fibre flocks.

A "resonator" refers to a spatial region in which a standing microwave field can propagate and can be an enclosed or substantially enclosed cavity resonator.

The fibre material whose density is measured is arranged in a spatial region 12a designated a "product space", which in operation of the sensor 12, 12', 12'', $12_1$ to $12_6$ is in a fixed spatial relationship with the spatial region of the resonator. The microwaves enter the product space in order to interact with the fibre material. The microwave resonator is permeable to the microwaves in the direction of the product space. The fibre material can be a continuous and/or unending product flow, for example fibre flocks in the form of a fibre/air flow 19, 21, 25', 25'', 33 or in the form of a flock layer 16 in spinning preparation machines, especially cleaning machines.

Although the foregoing invention has been described in detail by way of illustration and example for purposes of understanding, it will be obvious that changes and modifications may be practised within the scope of the appended claims.

What is claimed is:

1. The apparatus for determining the mass of textile fibre material in the form of fibre flocks, comprising:
    a measurement pathway configured to allow the fibre flocks to pass continuously therethrough;
    a measuring device comprising at least one microwave resonator for continuously measuring the passing fibre flocks in the measurement pathway; and
    an electronic control and regulation device coupled to the measuring device and configured to control a conveying device disposed downstream of the resonator based upon measurements of the fibre flocks effected by the measuring device.

2. The apparatus according to claim 1, wherein the measuring device is configured to measure moisture content of the passing fibre flocks.

3. The apparatus according to claim 1, wherein the measuring device is configured to compensate for moisture content when measuring the mass of the fibre flocks.

4. The apparatus according to claim 1, wherein a measurement value of the mass of the fibre flocks is used for open-loop control of at least one spinning preparation machine.

5. The apparatus according to claim 1, wherein a measurement value of the mass of the fibre flocks is used for closed-loop control of at least one spinning preparation machine.

6. The apparatus according to claim 1, wherein a measurement value of the mass of the fibre flocks is used for dispensing the fibre material in metered amounts in the course of feeding a spinning preparation machine.

7. The apparatus according to claim 1, wherein a measurement value of the mass of the fibre flocks is used in control of feeding a pneumatic flock-transporting device.

8. The apparatus according to claim 1, further comprising a flock feed device, the measurement device being arranged at an exit from the flock feed device.

9. The apparatus according to claim 8, wherein the flock feed device is selected from the group consisting of feed hoppers, condensers and flock charging shafts.

10. The apparatus according to claim 8, wherein the flock feed device includes at least one take-off roller.

11. The apparatus according to claim 10, wherein a speed of the at least one take-off roller is adjustable.

12. The apparatus according to claim 8, wherein the flock feed device is a hopper and has an inclined conveyor belt and a stripper roller.

13. The apparatus according to claim 12, wherein a speed of the inclined conveyor belt and/or the speed of the stripper roller is adjustable.

14. The apparatus according to claim 1, wherein the conveying device comprises a conveyor belt and the measurement device is associated with the conveyor belt.

15. The apparatus according to claim 14, wherein a speed of the conveyor belt is adjustable.

16. The apparatus according to claim 1, wherein the measurement pathway and the measurement device are so arranged that the fibre flocks pass through the microwave resonator in flight.

17. The apparatus according to claim 1, wherein the measurement pathway and the measurement device are so arranged that the fibre flocks fall through the microwave resonator.

18. The apparatus according to claim 1, wherein, for formation of a fibre blend, one or more devices for dispensing prespecifiable amounts of fibre flocks of different grades are provided.

19. The apparatus according to claim 18, further comprising a mixing apparatus having a plurality of charging shafts from which fibre flocks of each of the blend components can be deposited at a lower end of a respective charging shaft onto a mixing conveyor belt by at least one take-off roller.

20. The apparatus according to claim 19, wherein the mixing conveyor belt is arranged to be driven in a variable manner.

21. The apparatus according to claim 1, in wherein the measuring device is configured to continuously measure the fibre mass of the passing fibre flocks.

22. The apparatus according to claim 1, wherein, for mixing, closed-loop volumetric flow control is provided.

23. The apparatus according to claim 1, wherein a measurement value of the mass of the fibre flocks is arranged to be used for open-loop control and/or closed-loop control of a cleaning system having two or more cleaning machines.

24. The apparatus according to claim 1, wherein a measurement value of the mass of the fibre flocks is arranged to be used for open-loop control and/or closed-loop control of a carding system having at least one carding machine.

25. The apparatus according to claim 1, wherein a measurement value of the mass of the fibre flocks is arranged to be used for determining the through-flow rate in a pipeline for conveying fibre material.

26. The apparatus according to claim 1, wherein a measurement value of the mass of the fibre flocks is usable for determining production in a flock charging shaft.

27. The apparatus according to claim 1, wherein a measurement value of the mass of the fibre flocks is arranged to be used for determining production in a flock mixer or a flock feeder.

28. The apparatus according to claim 18, wherein mixing of the fibre flocks of different grades is carried out in a flow of air.

* * * * *

UNITED STATES PATENT AND TRADEMARK OFFICE
CERTIFICATE OF CORRECTION

PATENT NO. : 7,614,121 B2
APPLICATION NO. : 11/158016
DATED : November 10, 2009
INVENTOR(S) : Stefan Schlichter It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1002 days.

Signed and Sealed this

Nineteenth Day of October, 2010

David J. Kappos
*Director of the United States Patent and Trademark Office*